Figure 1:
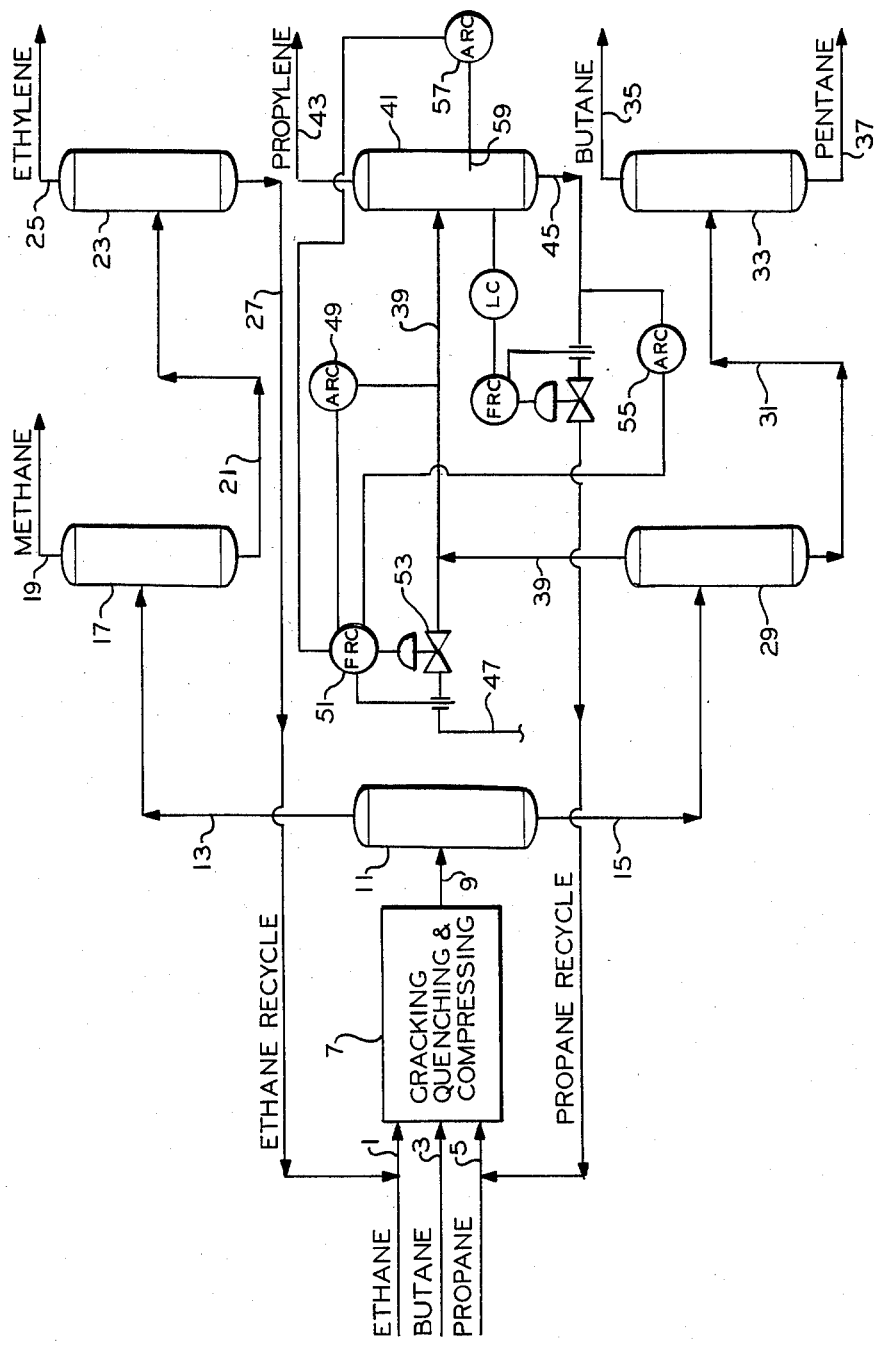

United States Patent [19]

Hampton

[11] Patent Number: 4,540,422
[45] Date of Patent: Sep. 10, 1985

[54] CONTROL OF THE CONCENTRATION OF METHYLACETYLENE AND PROPADIENE IN A PROPYLENE/PROPANE FRACTIONATION COLUMN

[75] Inventor: Joe B. Hampton, Bartlesville, Okla.

[73] Assignee: Phillips Petroleum Company, Bartlesville, Okla.

[21] Appl. No.: 601,762

[22] Filed: Apr. 18, 1984

[51] Int. Cl.³ ............................ F25J 3/02; B01D 3/42
[52] U.S. Cl. ........................................ 62/21; 62/20;
    62/32; 203/3; 203/6; 203/70; 585/867
[58] Field of Search ............... 62/21, 37, 44, 32, 20;
    203/3, 70, 6, 68; 585/648, 867, 809; 55/63;
    208/351, 356, 362

[56] References Cited

U.S. PATENT DOCUMENTS

| | | | |
|---|---|---|---|
| 2,371,860 | 3/1945 | Walls et al. | 203/70 |
| 3,229,471 | 1/1966 | Palen et al. | 62/21 |
| 3,390,535 | 7/1968 | Marshall | 585/867 |
| 3,616,267 | 10/1971 | McNeill et al. | 203/3 |
| 3,758,400 | 9/1973 | Hampton | 208/72 |
| 4,251,674 | 2/1981 | Callejas et al. | 585/272 |
| 4,345,105 | 8/1982 | Rogers | 585/648 |
| 4,371,718 | 2/1983 | Hutson | 203/70 |

FOREIGN PATENT DOCUMENTS 0753442  8/1980  U.S.S.R. ............................ 203/3

Primary Examiner—William F. Smith
Assistant Examiner—Andrew J. Anderson
Attorney, Agent, or Firm—A. W. Umphlett

[57] ABSTRACT

The concentration buildup of contaminants methylacetylene and propadiene in a propylene/propane fractionation column is prevented by controlling the injection of propane from a source external from the feedstream into the inlet stream to the column in response to the measured propane content of the feedstream downstream of the point of propane injection, the measured methylacetylene content of the bottoms product from the column, or the measured methylacetylene content of a sample from a tray of the column.

9 Claims, 1 Drawing Figure

CONTROL OF THE CONCENTRATION OF METHYLACETYLENE AND PROPADIENE IN A PROPYLENE/PROPANE FRACTIONATION COLUMN

BACKGROUND

This invention relates to a fractionation operation for separating propylene from propane. In one of its aspects this invention relates to a gas cracking and separating operation in which some of the separated products such as propane and ethane are recycled to the gas cracking operation. In another if its aspects this invention relates to the control of a fractionation operation by manipulation of feedstock to the fractionation. In still another aspect of this invention it relates to the addition of a component to the feedstock of a fractionation operation in response to the analyzed content of a specific compound in the fractionation process.

One of the problems encountered in a process of gas cracking of combination feedstocks of ethane, butane, and propane followed by compression and gas separation of the high pressure gas stream by a seriatim fractionation to separate the components of the gas stream by boiling point difference with recycle of some of the product streams to the gas cracking operation can be the buildup of unwanted materials in the various fractionation columns and product streams. Some of these unwanted components can actually prove to be of danger in the fractionation process or if recycled into the gas cracking operation. These unwanted components often provide problems in reaching specification limitations of product streams. In the fractionation to separate propylene from propane in a stream that has been recovered from de-ethanized and de-butanized gas cracking product the concentration of methylacetylene and propadiene in the bottoms from the fractionation increases proportionally as the concentration of propane in the feedstock decreases. Particularly when the propane stream is recycled to the gas cracking operation the high content of acetylenes is potentially explosively hazardous. The high content of methylacetylene and propadiene also makes the separation of propylene from the feed mixture more difficult without increasing the amount of methylacetylene and propadiene in the propylene product. Generally, the propylene product has a low specification limit for content of these compounds.

It has now been found that the controlled injection of propane from an outside source into the feedstream to increase the propane content in the separation column provides the necessary propane content in the bottoms product sufficiently to dilute methylacetylene and propadiene until the problems are eliminated. The present invention provides a method for controlling the injection of propane into the propylene/propane separation column feedstream.

It is therefore an object of this invention to provide a method for controlling the propane in the inlet to a propylene/propane separation column. It is also an object of this invention to inject a controlled amount of propane into the inlet stream of a propylene/propane separation column. It is another object of this invention to alleviate the buildup of methylacetylene and propadiene in the bottoms stream of a propylene/propane separation column. It is still another object of this invention in a gas cracking and separation system to provide a propane recycle stream to be used as at least a part of the feedstock in the gas cracking operation.

Other aspects, objects and the various advantages of this invention will become apparent upon reading the specification, studying the accompanying drawing, and reading the appended claims.

STATEMENT OF THE INVENTION

According to this invention a method is provided for controlling the propane in the inlet to a propylene/propane separation column by injecting propane into the inlet stream from a source external to the feedstream limiting the propane addition in response to the proportional content of a specific chemical component measured in a sample from the propylene/propane separation system.

In various embodiments of the invention the content of the component within the propylene/propane separation system which is measured to provide control of the propane addition can be chosen from among: (1) the propane content of the feedstream to the propylene/propane separation column with the content measured downstream of the point of propane injection; (2) the methlacetylene content of the bottoms product of the propylene/propane separation column; and (3) the methlacetylene content of a sample from a tray of the propylene/propane separation column.

In the preferred embodiment of this invention the propylene/propane separation column is part of a gas cracking, gas compression, gas separation operation in which the feedstream to the propylene/propane separation column is a de-ethanized and de-butanized product of a gas cracking operation and the bottoms product from the propylene/propane separation column is recycled as feedstock to the gas cracking operation.

The preferred operation of the invention is best understood in conjunction with the drawing which is a schematic representation of a gas cracking, compressing, and separating operation with emphasis on the propylene/propane separation column.

Referring now to the drawing, the general environment of the present invention will first be described followed by illustration of three specific aspects of the invention. The cracking, compression and separation of hydrocarbon feedstocks, particularly field gasses, is well known in the art. In the present invention a combination of ethane through line 1, butane through line 3, and propane through line 5 are fed into a gas cracking operation followed by quenching of the cracked gasses and compression of the mixed product of the gas cracking to a pressure of about 210 psia. In general, the conditions for the cracking, quenching and compression are well known in the art. The cracking, quenching and compressing are illustrated as 7 in the drawing. The conditions for the gas cracking generally will fall in the range of about 1500° F. with the quenching being a combination of heat transferred from the cracked gases in a heat exchanger to generate high pressure steam followed by contacting of the cracked gases with cooling water to reduce the reaction temperature below about 110° F. followed by compression in multiple stages.

The compressed, mixed product stream is passed through line 9 to de-ethanizing column 11 in which at conditions of about 180 psia, ethane and lighter gasses are separated as overhead product through line 13 and propane and heavier products are removed as a bottoms stream through line 15.

The deethanizer overhead stream is compressed and passed through line 13 to a demethanizing column 17 where under conditions of 450 psia methane is removed overhead through line 19 and a kettle product of ethane/ethylene is removed through line 21 as feedstock for separation in column 23 under conditions of 72 psia, and −96° F. into an overhead stream 25 of ethylene and a kettle product 27 of ethane with the ethane being recycled as gas cracking feedstock to line 1.

Kettle liquid from the de-ethanizing column 11 is removed through line 15 into the fractionation column 29 in which under conditions of 120 psia a separation is made to remove butanes and heavier products through line 31 as feedstock to a de-butanizing column 33 in which under conditions of 70 psia butane is removed as an overhead product through line 35 and pentane and heavier materials are removed as kettle product through line 37.

The overhead product from fractionating column 29 contains mostly propylene and propane with such contaminants as methylacetylene (MA) and propadiene (PD). The overhead is removed through line 39 as feedstock for the propylene/propane fractionation column 41. In this fractionation column under conditions of 255 psia the propylene is removed overhead through line 43 and propane is removed as kettle product through line 45 with recycle of the propane stream to line 5 as feedstock for the gas cracking. It is the operation of the propylene/propane fractionator that is of particular interest in the present invention. The present invention is concerned with a control of the addition of propane from an extraneous source from line 47 which feeds directly into feed stream 39 to provide a sufficient amount of propane in the propylene/propane separation system to allow the proper dilution of the contaminants, methylacetylene (MA) and propadiene (PD), to prevent their being carried overhead with the propylene stream and to prevent a possibly dangerous excess proportion of methylacetylene in the propane recycle, and also to prevent a dangerously high concentration of MA and PD in the lower sections of the fractionator.

The present invention provides three viable alternative methods for controlling the amount of propane that is added through line 47 into the feed stream 39 to the propylene/propane separation column 41. In the most preferred system an analyzer recorder controller 49 determines the amount of propane plus methylacetylene in the feed stream line 39 and flow recorder controller 51 operates motor valve 53 in response to the signal generated by analyzer recorder controller 49 to control the propane injected through 47 so that the amount of propane plus methylacetylene in the feed stream 39 is maintained within prescribed limits. In the preferred operation of this invention the propane is maintained within a range of about 25 percent to about 30 percent in the feed stream.

In an alternative method of control an analyzer recorder controller 55 determines the methylacetylene plus propadiene content in the bottoms product passing through line 45 and generates a signal that controls through flow recorder controller 51 the amount of propane passed by line 47 through control valve 53 into the feed stream 39. In this alternative operation of the invention the methylacetylene and propadiene content is maintained within a range of 2 percent to 6 percent.

In a third alternative analyzer recorder controller 57 determines the methylacetylene plus propadiene content on a tray 59 of the separation column and generates a signal to which flow recorder controller 51 responds to control the flow of propane from line 47 through control valve 53 into the feed stream 39. In a preferred operation the methylacetylene plus propadiene content is controlled according to the position of the tray within the separation column from which the sample is taken. Typically the value for content of methylacetylene plus propadiene in the lower portion of the column is 14 percent.

I claim:

1. A method for separating propylene/propane mixtures containing methylacetylene and propadiene contaminants in a fractionation column comprising controlling the concentration of methylacetylene and propadiene in the column by injecting propane into the inlet stream from a source external to the feedstream with control of the propane addition in response to the measured propane content of the feedstream downstream of the point of propane injection.

2. A method of claim 1 wherein the feed stream to the propylene/propane fractionation column is a de-ethanized and de-butanized product of a gas cracking operation.

3. A method of claim 2 wherein the bottoms product for the propylene/propane fractionation column is recycled as feedstock to a gas cracking operation.

4. A method for separating propylene/propane mixtures containing methylacetylene and propadiene contaminants in a fractionation column comprising controlling the concentration of methylacetylene and propadiene in the column by injecting propane into the inlet stream from a source external to the feedstream with control of the propane addition in response to the measured methylacetylene content of the bottoms product from the propylene/propane fractionation column.

5. A method of claim 4 wherein the feed stream to the propylene/propane fractionation column is a de-ethanized and de-butanized product of a gas cracking operation.

6. A method of claim 5 wherein the bottoms product from the propylene/propane fractionation column is recycled as feedstock to a gas cracking operation.

7. A method for separating propylene/propane mixtures containing methylecetylene and propadiene contaminants in a fractionation column comprising controlling the concentration of methylacetylene and propadiene in the column by injecting propane into the inlet stream from a source external to the feedstream with control of the propane addition in response to the measured methylacetylene content of a sample from a tray of the propylene/propane fractionating column.

8. A method of claim 7 wherein the feed stream to the propylene/propane fractionation column is a de-ethanized and de-butanized product of a gas cracking operation.

9. A method of claim 8 wherein the bottoms product from the propylene/propane fractionation column is recycled as feedstock to a gas cracking operation.

* * * * *